(12) United States Patent
Venkataraman et al.

(10) Patent No.: US 11,026,561 B2
(45) Date of Patent: Jun. 8, 2021

(54) METHOD AND SYSTEM FOR AUTOMATICALLY REPOSITIONING A VIEWABLE AREA WITHIN AN ENDOSCOPE VIDEO VIEW

(71) Applicant: Verb Surgical Inc., Mountain View, CA (US)

(72) Inventors: Jagadish Venkataraman, Menlo Park, CA (US); Dave Scott, Oakland, CA (US); Eric Johnson, Pacific Grove, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 0 days.

(21) Appl. No.: 16/361,075

(22) Filed: Mar. 21, 2019

(65) Prior Publication Data

US 2020/0304753 A1 Sep. 24, 2020

(51) Int. Cl.
*A61B 1/00* (2006.01)
*H04N 7/01* (2006.01)
(Continued)

(52) U.S. Cl.
CPC ...... *A61B 1/00055* (2013.01); *A61B 1/00045* (2013.01); *A61B 1/3132* (2013.01);
(Continued)

(58) Field of Classification Search
CPC ...... H04N 7/0117; H04N 7/183; A61B 34/30; A61B 90/37; A61B 1/00045;
(Continued)

(56) References Cited

U.S. PATENT DOCUMENTS

| 2012/0083652 A1* | 4/2012 | Langlois ............ A61B 1/00055 |
| | | 600/103 |
| 2014/0099066 A1* | 4/2014 | Jang ...................... G09G 5/006 |
| | | 386/230 |

(Continued)

FOREIGN PATENT DOCUMENTS

| JP | 2003210414 | 7/2003 |
| JP | 2005334090 | 12/2005 |

(Continued)

OTHER PUBLICATIONS

International Search Report and Written Opinion dated Dec. 30, 2019 for International Application No. PCT/US2019/025673, 11 pages.

*Primary Examiner* — John R Schnurr
(74) *Attorney, Agent, or Firm* — Womble Bond Dickinson (US) LLP

(57) ABSTRACT

Embodiments described herein provide various examples of displaying video images of a surgical video captured at a first resolution on a screen of a surgical system having a second resolution lower than the first resolution. In one aspect, a process begins by receiving the surgical video and selecting a first portion of the video images having the same or substantially the same resolution as the second resolution. The process subsequently displays the first portion of the video images on the screen. While displaying the first portion of the video images, the process monitors a second portion of the video images not being displayed on the screen for a set of predetermined events, wherein the second portion is not visible to the user. When a predetermined event in the set of predetermined events is detected in the second portion, the process generates an alert to notify the user.

18 Claims, 8 Drawing Sheets

(51) Int. Cl.
*G06K 9/00* (2006.01)
*H04N 7/18* (2006.01)
*A61B 90/00* (2016.01)
*A61B 1/313* (2006.01)
*A61B 34/30* (2016.01)

(52) U.S. Cl.
CPC .............. *A61B 34/30* (2016.02); *A61B 90/37* (2016.02); *G06K 9/00718* (2013.01); *H04N 7/0117* (2013.01); *H04N 7/183* (2013.01); *A61B 2090/373* (2016.02); *G06K 2009/00738* (2013.01)

(58) Field of Classification Search
CPC ............ A61B 1/3132; A61B 2090/373; A61B 1/00055; G06K 9/00718; G06K 2009/00738
See application file for complete search history.

(56) References Cited

U.S. PATENT DOCUMENTS

2016/0345802 A1* 12/2016 Nir ........................ G02B 23/243
2017/0367559 A1* 12/2017 Takahashi .............. A61B 5/743
2018/0228557 A1* 8/2018 Darisse .............. A61B 1/00149
2019/0053857 A1* 2/2019 Sugie ................ A61B 1/00188
2019/0231444 A1* 8/2019 Tojo .................... A61B 1/0005

FOREIGN PATENT DOCUMENTS

JP          5148022        2/2013
KR       20180136857     12/2018

* cited by examiner

METHOD AND SYSTEM FOR AUTOMATICALLY REPOSITIONING A VIEWABLE AREA WITHIN AN ENDOSCOPE VIDEO VIEW

TECHNICAL FIELD

The present disclosure generally relates to visualization and user interface technology for displaying endoscopy videos and, more specifically, to systems, devices and techniques for displaying high-resolution endoscopy videos on lower-resolution display devices.

BACKGROUND

Driven by the rapid growth of video and imaging technology, endoscope technology continues to evolve to allow capturing increasingly higher resolution endoscope videos and still images. Presently, endoscope systems with full HD resolution (i.e., 1080p) have become widely available and highly affordable. Some advanced endoscope systems are even capable of capturing videos at ultra-high definition (UHD) resolutions such as at 4K resolution, making the captured endoscopic image qualities rival human vision in open surgeries.

However, in many operating rooms, the displays/monitors assisting surgeons performing endoscopy procedures are not fully compatible with the captured endoscope image resolutions. For example, a typical HD monitor having a native resolution of 1920px×1080p cannot display higher resolution images, such as UHD images, without downsampling the images first to its native resolution. Unfortunately, displaying downsampled video images on a display/monitor can have a number of undesirable effects. One of these undesirable effects is the "black border" effect when the downsampled video images do not occupy the full display area of the monitor. This effect typically arises when the display aspect ratio is greater than the video-image aspect ratio. For example, to display downsampled 2560px×2160p endoscope images on a full HD display of 1920px×1080p native resolution, the downsampled video images may have a 1280px×1080p resolution after mapping each 2×2 block of pixels of 2560px×2160p images into a single pixel (e.g., using average/medium of each of the RGB or YCbCr channels). However, displaying 1280px×1080p images on a 1920px×1080p display results in a rather large black border on either side of the display with the downsampled video images only being shown in the display area between the two black borders. Although these black borders can be used to display some surgical-related information such as user-interface (UI)-related icons, such information shown on the display screen can cause various degrees of distraction to the surgeons performing the surgical procedures.

SUMMARY

This patent disclosure provides various embodiments of displaying high-resolution endoscopy videos on a display device having a screen of a lower native resolution. In some embodiments, the disclosed visualization system allows for displaying a portion of the full-resolution endoscope video centered around a region-of-interest (ROI), such as the tip of a surgical tool, on the lower-resolution display device. Moreover, the portion of the full-resolution endoscope video, which can have the same or substantially the same resolution as the native resolution of the display device being displayed, is displayed at its original resolution without being downsampled, thereby providing the user with an immersive viewing experience.

In some embodiments, while displaying a portion of the full-resolution endoscope video on the display device having a lower-resolution screen, the displayed portion of the full-resolution endoscope video can be changed from a current ROI of the full-resolution endoscope video to a new ROI of the full-resolution endoscope video. In various embodiments, the new ROI can be determined based on a detected surgical event within the endoscope video, a movement of a surgical tool within the endoscope video, or based on detecting a change of user's gaze on the display screen. In this manner, the full resolution of the display screen serves as a "viewing window," which selectively displays different regions of the full-resolution endoscope video having the same size as the display screen for the user to view.

Note that the disclosed visualization system creates an on-screen/visible portion of the full-resolution endoscope video (i.e., within the viewing window) and an off-screen/non-visible portion of the full-resolution endoscope video (i.e., outside of the viewing window). In some embodiments, while displaying a portion of the full-resolution endoscope video, the disclosed visualization system can monitor the off-screen/non-visible portion of the full-resolution endoscope video to detect specific surgical events, such as complications taking place within the off-screen portion of the full-resolution endoscope video. For example, the disclosed visualization system can use a machine-learning-based and/or computer-vision-based technique on the off-screen portion of the video images to perform surgical event detections. If such an event is detected in the off-screen portion, the disclosed system can automatically notify the surgeon that such an event is taking place and direct the surgeon to the off-screen location associated with the detected event. In some embodiments, the off-screen surgical events that can be monitored can include, but are not limited to: surgical complications, such as surgical smoke and bleeding; states of surgical tools that are off-screen, such as whether the jaws of a surgical tool are closed or open; and risks to critical anatomies off-screen, e.g., an off-screen critical organ getting too close to a sharp surgical tool.

In some embodiments, while displaying a portion of the full-resolution endoscope video on the display device with a lower-resolution screen, the disclosed visualization system can monitor and track the movement of a surgical tool (e.g., the tip of the tool) within the viewing window. For example, the disclosed visualization system can use a machine-learning-based and/or computer-vision-based technique on the on-screen portion of the video images to perform tool monitoring and tracking functionality. If the system detects that the tool tip is about to go off-screen, the system can automatically adjust/reposition the viewing window within the full-resolution endoscope video to keep the tool tip on the screen and visible, thereby preventing the surgeon from having to manually adjust the location of the viewing window or the endoscope camera inside the patient to keep the tool tip on the screen. In some embodiments, the disclosed system can combine the above-described tool-tracking functionality and an eye-tracking functionality to determine the focal point of the user's eyes (i.e., the gaze) on the display screen. The disclosed system can also adjust the viewing window within the full-resolution endoscope video by following the movement of the user's gaze, so that the viewing window can be centered around the location of the user's gaze. This technique also allows the user to move the viewing window within the full-resolution endoscope video by simply changing the gaze.

In some embodiments, while displaying a portion of the full-resolution endoscope video on the display device with a lower-resolution screen, the disclosed visualization system allows the user to manually adjust the viewing window within the full-resolution endoscope video from one ROI to another ROI without having to move the endoscope inside the patient. In particular, the disclosed visualization system can be configured to allow the user to use one or more user interface devices (UIDs), such as a foot pedal and/or a hand controller to move the viewing window to a new ROI within the endoscope video. In doing so, the new region of display continues to occupy the full viewing window to provide the surgeon with an immersive viewing experience without creating any black border space on either side of the screen.

In one aspect, a process for displaying video images of a surgical video captured at a first resolution on a screen of a surgical system having a second resolution lower than the first resolution is disclosed. This process can begin by selecting a first portion of the video images having the same or substantially the same resolution as the second resolution. The process subsequently displays the first portion of the video images on the screen. While displaying the first portion of the video images, the process also monitors a second portion of the video images not being displayed on the screen for a set of predetermined events. This second portion of the video images is not visible to the user. When a predetermined event in the set of predetermined events is detected in the second portion of the video images, the process generates an alert to notify the user that an off-screen event has been detected.

In some embodiments, the first resolution is greater than the second resolution in both the horizontal and the vertical dimensions. Moreover, the first portion of the video images is substantially the center portion of the video images.

In some embodiments, the process selects the first portion of the video image by selecting a portion of the video image centered on a tip of a surgical tool captured by the video images.

In some embodiments, while displaying the first portion of the video images, the first portion of the video images occupies the full display area of the screen without leaving any blank space on the screen.

In some embodiments, the process monitors the second portion of the video images for the set of predetermined events by using one or more machine-learning models to process the second portion of the video images in order to detect each of the set of predetermined events.

In some embodiments, the process generates the alert to notify the user that an off-screen event has been detected by displaying a warning message on the screen to prompt the user to take appropriate action.

In some embodiments, the alert on the screen includes a direction indicator to show the user a direction in which the off-screen event was detected.

In some embodiments, when the off-screen event is detected, the process immediately changes the view on the screen from the first portion of the video images to a third portion of the video images, which contains the detected off-screen event.

In some embodiments, the third portion of the video images overlaps with the first portion and the second portion of the video images and has the same size as the first portion of the video images.

In some embodiments, when the off-screen event is detected, the process immediately changes the view on the screen from the first portion of the video images to the full video images displayed at a reduced resolution to make the detected off-screen event visible to the user.

In some embodiments, after generating the alert to notify the user that an off-screen event has been detected, the process further includes the steps of: (1) providing the user with a selection option to either change the view on the screen from the first portion of the video images to another portion of the video images containing the detected off-screen event or change the view on the screen from the first portion of the video images to the full video images displayed at a reduced resolution; (2) receiving a user selection in response to the selection option; and (3) changing the view on the screen based on the received user selection to make the detected off-screen event visible to the user.

In some embodiments, after generating the alert to notify the user that an off-screen event has been detected, the process allows the user to manually change the view on the screen from the first portion of the video images to another portion of the video images containing the detected off-screen event in response to the alert.

In some embodiments, the set of predetermined events includes surgical smoke and bleeding.

In some embodiments, the set of predetermined events includes a set of surgical tool-related events, which further includes: (1) whether the jaws of a surgical tool detected off-screen are closed or open; and (2) whether a tip of a surgical tool detected off-screen is too close to a critical anatomy.

In some embodiments, if the detected predetermined event is one of the set of surgical tool-related events, the process immediately deactivates functionalities or locking motion of a surgical tool associated with the detected surgical tool-related event.

In some embodiments, the surgical video is one of: an endoscopic surgery video; a laparoscopic surgery video; a robotic surgery video; and an open surgery video.

In another aspect, a system for displaying a surgical video is disclosed. This system can include: one or more processors; and a screen having a native resolution. Moreover, the one or more processors are configured to: receive a surgical video comprising a sequence of video images captured at a first resolution for display on the screen, wherein the first resolution is greater than the native resolution of the screen; for each video image in the sequence of video images, select a first portion of the video image having the same or substantially the same resolution as the native resolution to display on the screen; while displaying the first portion of the video images, monitor a second portion of the video images not being displayed on the screen for a set of predetermined events, wherein the second portion of the video images is not visible to the user; and if a predetermined event in the set of predetermined events is detected in the second portion of the video images, generate an alert to notify the user that an off-screen event has been detected.

In some embodiments, when the off-screen event is detected, the one or more processors are further configured to immediately change the view on the screen from the first portion of the video images to a third portion of the video images, which contains the detected off-screen event. Alternatively, when the off-screen event is detected, the one or more processors can be further configured to immediately change the view on the screen from the first portion of the video images to the full video images displayed at a reduced resolution to make the detected off-screen event visible to the user.

In some embodiments, after generating the alert to notify the user that an off-screen event has been detected, the one or more processors are further configured to: provide the user with a selection option to either change the view on the screen from the first portion of the video images to another portion of the video images containing the detected off-screen event or change the view on the screen from the first portion of the video images to the full video images displayed at a reduced resolution; receive a user selection in response to the selection option; and change the view on the screen based on the received user selection to make the detected off-screen event visible to the user.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1:
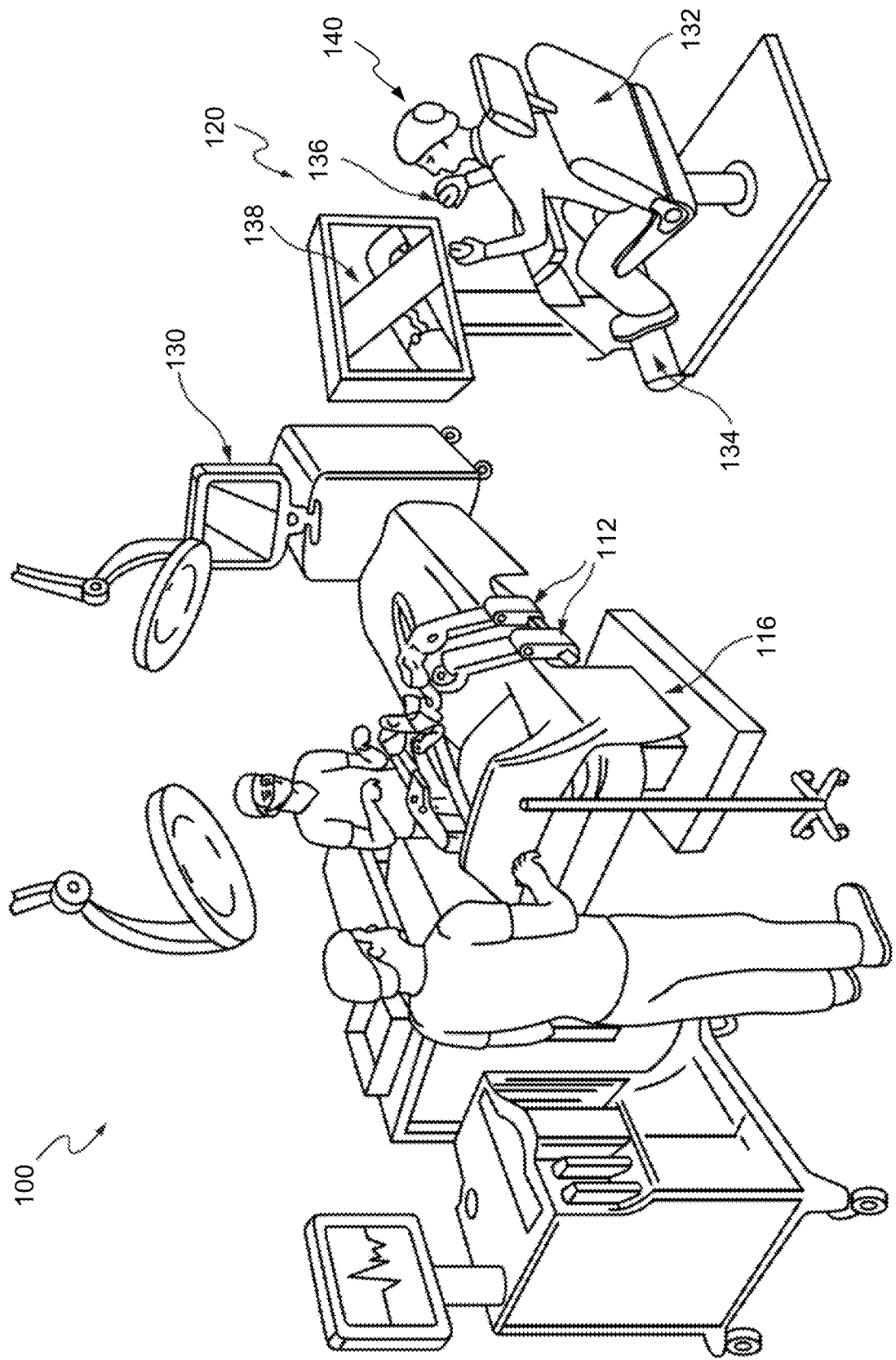
FIG. 1 shows a diagram illustrating an exemplary operating room environment with a robotic surgical system for implementing the disclosed visualization system in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures that involve displaying and capturing video images of the surgical procedures. For example, almost all minimally invasive procedures, such as endoscopy, laparoscopy, and arthroscopy, involve using video cameras and video images to assist the surgeons. Furthermore, state-of-the-art robotic-assisted surgeries require intraoperative video images being captured and displayed on the monitors for the surgeons. Consequently, for many of the aforementioned surgical procedures, e.g., a gastric sleeve or prostatectomy, a large cache of surgical videos already exists and continues to be created as a result of a large number of surgical cases performed by many different surgeons from different hospitals. The simple fact of the existence of a huge (and constantly increasing) number of surgical videos of a particular surgical procedure allows for processing and analyzing the surgical videos of the given procedure using machine-learning-based approaches.

This patent disclosure provides various embodiments of displaying high-resolution endoscopy videos on a display device having a screen of a lower native resolution. In some embodiments, the disclosed visualization system allows for displaying a portion of the full-resolution endoscope video centered around a region-of-interest (ROI), such as the tip of a surgical tool, on the lower-resolution display device. Moreover, the portion of the full-resolution endoscope video, which can have the same or substantially the same resolution as the native resolution of the display device being displayed, is displayed at its original resolution without being downsampled, thereby providing the user with an immersive viewing experience.

In some embodiments, while displaying a portion of the full-resolution endoscope video on the display device having a lower-resolution screen, the displayed portion of the full-resolution endoscope video can be changed from a current ROI of the full-resolution endoscope video to a new ROI of the full-resolution endoscope video. In various embodiments, the new ROI can be determined based on a detected surgical event within the endoscope video, a movement of a surgical tool within the endoscope video, or detecting a change of user's gaze on the display screen. In this manner, the full-resolution of the display screen serves as a "viewing window," which selectively displays different regions of the full-resolution endoscope video having the same size as the display screen for the user to view.

Note that the disclosed visualization system creates an on-screen/visible portion of the full-resolution endoscope video (i.e., within the viewing window) and an off-screen/non-visible portion of the full-resolution endoscope video (i.e., outside of the viewing window). In some embodiments, while displaying a portion of the full-resolution endoscope video, the disclosed visualization system can monitor the off-screen/non-visible portion of the full-resolution endoscope video to detect specific surgical events, such as complications taking place within the off-screen portion of the full-resolution endoscope video. For example, the disclosed visualization system can use a machine-learning-based and/or computer-vision-based technique on the off-screen portion of the video images to perform surgical event detection. If such an event is detected in the off-screen portion, the disclosed system can automatically notify the surgeon that such an event is taking place and direct the surgeon to the off-screen location associated with the detected event. In some embodiments, the off-screen surgical events that can be monitored can include, but are not limited to: surgical complications, such as surgical smoke and bleeding; states of surgical tools that are off-screen, such as whether the jaws of a surgical tool are closed or open; and risks to critical anatomies off-screen, e.g., an off-screen critical organ getting too close to a sharp surgical tool.

In some embodiments, while displaying a portion of the full-resolution endoscope video on the display device with a lower-resolution screen, the disclosed visualization system can monitor and track the movement of a surgical tool (e.g., an end effector or a tip of the tool) within the viewing window. For example, the disclosed visualization system can use a machine-learning-based and/or computer-vision-based technique on the on-screen portion of the video images to perform tool monitoring and tracking functionality. If the system detects that the tool tip is off-center, close to an edge of the screen, or about to go off-screen, the system can automatically adjust/reposition the viewing window within the full-resolution endoscope video to keep the tool tip visible and at the center of the screen, thereby preventing the surgeon from having to manually adjust the location of the viewing window or the endoscope camera inside the patient to keep the tool tip on the screen. In some embodiments, the disclosed system can combine the above-described tool-tracking functionality and an eye-tracking functionality to determine the focal point of the user's eyes (i.e., the gaze) on the display screen. The disclosed system can also adjust the viewing window within the full-resolution endoscope video by following the movement of the user's gaze, so that the viewing window can be centered around the location of the user's gaze. This technique also allows the user to move the viewing window within the full-resolution endoscope video by simply changing the gaze.

In some embodiments, while displaying a portion of the full-resolution endoscope video on the display device with a lower-resolution screen, the disclosed visualization system allows the user to manually adjust the viewing window within the full-resolution endoscope video from one ROI to another ROI without having to move the endoscope inside the patient. In particular, the disclosed visualization system can be configured to allow the user to use one or more user interface devices (UIDs) and/or one or more foot pedals to move the viewing window to a new ROI within the endoscope video. In doing so, the new region of display continues to occupy the full viewing window to provide the surgeon with an immersive viewing experience without creating any black border space on either side of the screen.

FIG. 1 shows a diagram illustrating an exemplary operating room environment with a robotic surgical system 100 for implementing the disclosed visualization system in accordance with some embodiments described herein. As shown in FIG. 1, robotic surgical system 100 comprises a surgeon console 120, a control tower 130, and one or more surgical robotic arms 112 located at a robotic surgical platform 116 (e.g., a table or a bed etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., teleoperation). User console 120 may be located in the same operating room as robotic surgical system 100, as shown in FIG. 1. In other environments, user console 120 may be located in an adjacent or nearby room, or teleoperated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to achieve anesthesia. Initial access to the surgical site may be performed manually with robotic surgical system 100 in a stowed or withdrawn configuration to facilitate access to the surgical site. Once the access is achieved, initial positioning and/or preparation of the robotic system may be performed. During the procedure, a surgeon in the user console 120 may use the foot-operated controls 134 and/or UIDs 136 to manipulate various surgical tools/end effectors and/or imaging systems to perform the surgery. Manual assistance may also be provided at the procedure table by sterile-gowned personnel, who may perform tasks including, but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures including, but not limited to, robotic surgical system 100 cleaning and/or sterilization, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit them to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

In some embodiments, the disclosed visualization system for displaying high-resolution endoscopy videos on display devices with lower-resolution screens can be implemented on control tower 130 to control the display of the captured endoscopy videos from robotic surgical platform 116 on user display 138, which may have a lower resolution than the captured endoscopy videos. Moreover, other disclosed functionalities of the proposed visualization system, such as off-screen event detection can be performed on control tower 130. Note that while FIG. 1 describes a robotic surgical system for implementing the disclosed visualization system, the application of the disclosed visualization system is not limited to robotic surgical systems. Generally, the disclosed visualization system and its associated techniques can be used within any surgical procedures that involve capturing and displaying video images of the surgical procedures can employ. For example, these surgical procedures can include almost all minimally invasive procedures, such as endoscopy, laparoscopy, and arthroscopy, which involve using video cameras and video images to assist the surgeons. We now describe the disclosed visualization system in more detail below.

In some embodiments, when the native resolution of a display screen of the display device (or simply the "display," the "screen" or the "display screen" hereinafter, which are used interchangeably) is less than the image resolution of an endoscope video, the disclosed visualization system can use the full resolution of the display screen to display a portion/region of the full-resolution endoscope video at its original resolution, creating an effect of placing a viewing window of the native resolution inside the full-resolution endoscope video. For example, if the native resolution of a display screen is 1920px×1080p, to display high-resolution video images of 2560px×2160p resolution, the disclosed visualization system is configured to select just a 1920px×1080p portion (e.g., the center portion) of the 2560px×2160p video images to be displayed on the screen. In doing so, the disclosed system can take advantage of the full screen resolution of the display screen and the high-resolution nature of the video images to provide the user, such as a surgeon 140 in robotic surgical system 100, with a full immersive viewing experience.

Figure 2A:
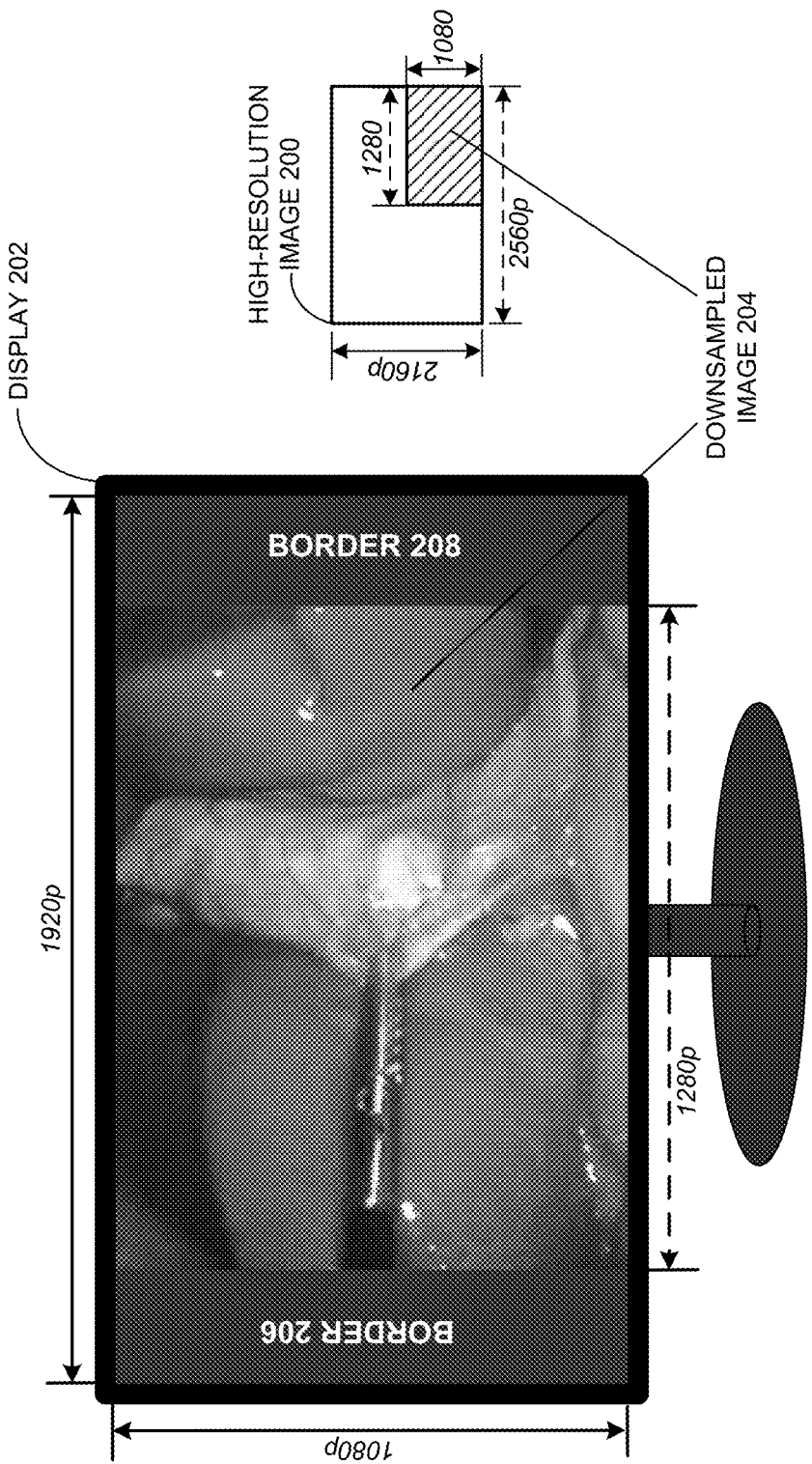
FIG. 2A shows an exemplary visualization solution for displaying a high-resolution endoscope video image of 2560px×2160p resolution on a display of 1920px×1080p native resolution in accordance with some embodiments described herein.

FIG. 2A shows an exemplary visualization solution for displaying a high-resolution endoscope video image 200 of 2560px×2160p resolution on a display 202 of 1920px×1080p native resolution in accordance with some embodiments described herein. In the embodiment shown, to fit the entire 2560px×2160p image 200 into display 202, which has a much lower resolution than the image being displayed, the high resolution image 200 is first downsampled by mapping each 2×2 block of pixels of the 2560px×2160p image into a single pixel, which subsequently generates a downsampled image 204 of 1280px×1080p resolution (illustrated as the shaded area within the inset image in FIG. 2A). In some embodiments, downsampling high-resolution image 200 involves computing the average/medium of each 2×2 block for each of the RGB or YCbCr channels of the 2560px×2160p image. The downsampled image 204, which has a lower resolution than the native resolution of display 202, can then be displayed in its entirety on display 202.

As can be seen in FIG. 2A, when displaying downsampled image 204 within display 202, the vertical resolution of downsampled image 204 can fit in the full extent of display 202. This display option would allow the surgeon to always see the entire endoscope video (also referred to as "endoscope view" hereinafter) without ever missing an event taking place within the full endoscope view. For this reason, the visualization solution for the high-resolution image or video depicted in FIG. 2A is also referred to as the "full-image-view mode" below. However, the horizontal resolution of downsampled image 204 only takes up the center region of display 202, thereby creating empty border regions 264 and 208. Although one can use the border regions 206 and 208 to display relevant surgical information, such a one-screen display can feel like an annoyance or distraction to some users/surgeons when viewing the downsampled video images on display 202. Moreover, plenty of detailed/useful information in the original 2560px×2160p resolution image 200 is lost in the downsampled image 204 shown on display 202.

Figure 2B:
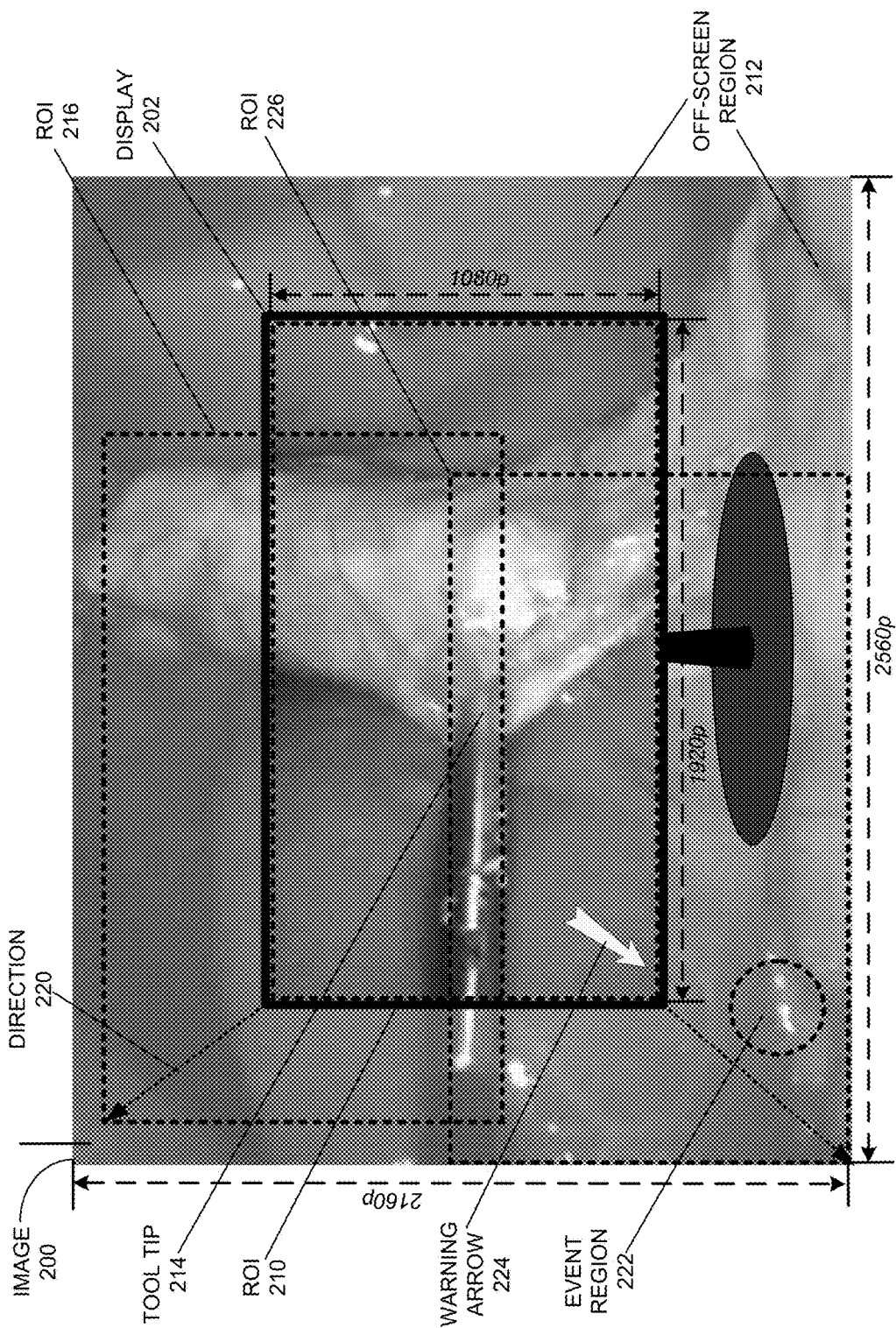
FIG. 2B shows an exemplary visualization solution for displaying the same high-resolution video image of 2560px×2160p resolution on the display of 1920px×1080p native resolution without downsampling the high-resolution image in accordance with some embodiments described herein.

FIG. 2B shows an exemplary visualization solution for displaying the same high-resolution video image 200 of 2560px×2160p resolution on display 202 of 1920px×1080p native resolution without downsampling the high-resolution image 200 in accordance with some embodiments described herein. In this embodiment, the disclosed visualization system first selects a region of interest (ROI) 210 of 1920px×1080p in resolution/size from the original 2560px×2160p image 200, and subsequently extracts and displays the selected ROI 210 on display 202. As shown in FIG. 2B, because the extracted ROI 210 (shown by a dashed rectangular box overlapping the display border of display 202) is identical in size to the display resolution, when displaying ROI 210 on display 202, ROI 210 takes up the entire 1920px×1080p display area without leaving any blank space. Note that this display technique separates high-resolution video image 200 into an on-screen/visible region, i.e., ROI 210 and an off-screen/non-visible region 212 outside of ROI 210. Off-screen region 212, which surrounds ROI 210, is intentionally grayed out to indicate that it is not visible to a user when ROI 210 is being displayed. In the embodiment shown in FIG. 2B, ROI 210 is selected and extracted from substantially the center region of the original video image 200. In other embodiments, ROI 210 can be selected so that it is centered on a tip of a surgical tool captured in video image 200, such as tool tip 214. In such embodiments, an image processing technique with tool detection and recognition functions (e.g., a machine-learning-based or a computer-vision-based technique) can be used to first detect the tool and subsequently determine the location of tool tip 214. However, if no tool is initially detected in image 200, the system can simply select and extract the center portion of image 200 as the initial ROI 210.

Using the partial-image-view (or "partial-view" hereinafter) technique of FIG. 2B, each high-resolution video image 200 is divided into an on-screen portion that is visible to the user and an off-screen portion that is not visible to the user. The user looking at display 202 gets an immersive viewing experience of the on-screen portion of the high-resolution video image 200 at its original resolution, which fills up the entire 1920px×1080p screen resolution, without any of the annoying blank space on either side of the displayed partial image. Note that during an active surgical procedure, any event taking place within the on-screen portion of the full-resolution endoscope video can be directly observed by the user at its original resolution to trigger a proper response from the user. However, without the complete view of the full-resolution endoscope video, an event taking place within the off-screen region 212 of the video image 202 cannot be instantly observed by the user.

In the discussion below, the visualization technique depicted in FIG. 2B is also referred to as the "partial-immersive-view technique" because a portion of the high-resolution image is selected and displayed at its original resolution on a display having the same or substantially the same resolution as the portion of the high-resolution image, providing the user with an immersive viewing experience. Similarly, the visualization solution for the high-resolution image 200 and the associated high-resolution video as depicted in FIG. 2B is also referred to as the "partial-immersive-view mode" below, which is in contrast to the full-image-view mode described above.

In some embodiments, when using the partial-immersive-view technique to selectively access a portion of the high-resolution video images without downsampling, a user can manually navigate among the high-resolution video images to cause different portions of the high-resolution video images to be displayed on the screen and become visible to the user. In other words, the full display screen serving as the "viewing window" can be "moved" around within the boundary of the full endoscope view so that the user can monitor different portions of the high-resolution video images (e.g., of an endoscope video). For example, within robotic surgery system 100 described in FIG. 1, surgeon 140 at the surgeon bridge/console 120 can use UIDs 136, a foot pedal, or a combination of the UIDs and foot pedal, to reposition the viewing window within the full endoscope video. Referring to FIG. 2B for example, allowing the user to manually navigate within the full 2560px2160p resolution image 200 can enable the user to change the location of the 1920px1080p display area (i.e., the viewing window) to any portion of full 2560px2160p image 200. For example, the user can manually adjust the viewing window from the initial ROI 210 at the center of video image 200 to ROI 216 (i.e., the dashed rectangular box 216) at the upper left portion of the video image 200 along the direction 220. Using this manual navigation technique, any portion of the full-resolution endoscope video is accessible to the user even though only one portion of the full-resolution video can be displayed/viewed at any given time.

In some embodiments, the full-image-view technique of FIG. 2A and partial-immersive-view technique of FIG. 2B can be combined to provide a user with a mechanism to switch between these two viewing modes on a display. For example, the disclosed visualization system may begin to show the endoscope video in full-image-view mode to provide the user with an overview of the anatomy and tool placement/status at a reduced resolution. This display mode also allows the user to view surgical-procedure-related information displayed in the border regions (e.g., borders 206 and 208) on the screen. Next, when the user wants to focus on the end effector or tool-tip action at full resolution, the user can use UIDs, a foot pedal, or a combination thereof, to toggle the display model to the partial-immersive-view mode, e.g., by interacting with a designated icon on the display.

In some embodiments, before switching the display/viewing mode, the user can also physically adjust the endoscope inside the patient so that the tip of the tool is substantially at the center of the endoscope view. Hence, if the disclosed system automatically selects the center portion of the full endoscope video for display in the partial-immersive-view mode, the corresponding partial-immersive-view, i.e., the display, can remain centered on the tip of tool after the display mode has been switched. In other embodiments, however, the user does not need to physically adjust the endoscope to center on the tool tip before switching the display mode. Instead, the disclosed system can apply a computer vision or a machine learning operation to automatically locate the tool tip in the full endoscope video. Next, when the user chooses to switch the display mode, the system automatically selects and displays the portion of the video images that are centered on the determined tool tip location in the partial-immersive-view mode. After a period of time working in the partial-immersive-view mode, if the user decides to switch back to the full-image-view mode, the user can again manually (e.g., by interacting with the designated icon on the display) exit the partial-immersive-view mode and return to the full-image-view mode.

Note that when a surgeon performs a surgical procedure in the partial-immersive-view mode, even if the surgeon has the option to navigate to another portion of the full endoscope view, and the option to switch back and forth between the partial-immersive-view mode and the full-image-view mode, the surgeon still cannot see the off-screen portion of the full-resolution video images during the time period associated with the partial-immersive-view mode. As a result, the surgeon may not be able to react, or react fast enough, to an event taking place in the off-screen portion of the video images that requires the attention or immediate action of the surgeon.

Hence, this patent disclosure also provides various embodiments of an off-screen video image processing technique that can process the high-resolution video images in the background independently of displaying the selected portion/ROI of the high-resolution video images on the screen. More specifically, while displaying a high-resolution endoscope video in the partial-immersive-view mode, the disclosed system can also run one or more monitoring programs in the background that are designed to detect a set of predetermined events in the off-screen region (e.g., off-screen region 212) of the video images. In some embodiments, each of the monitoring programs can use a computer-vision-based technique or a deep-learning (DL)-based technique, or a combination of both. In some embodiments, the predetermined events that can be detected within the off-screen portion of the video images can include surgical complications such as bleeding or surgical smoke, which would often require the immediate attention of the surgeon performing the procedure in the partial-immersive-view mode. For example, if a patient is bleeding off-screen and the surgeon does not realize this event is happening, the disclosed system can automatically notify the surgeon that this bleeding event is taking place and direct the surgeon to the event location.

In some embodiments, multiple DL models can be constructed such that each of the DL models is used to detect a particular type of surgical complication. In other embodiments, a single DL model can be constructed to simultaneously detect two or more types of surgical complications including bleeding and surgical smoke. In various embodiments, each of the DL models for detecting complication events can include a regression model, a deep neural network-based model, a support vector machine, a decision tree, a Naive Bayes classifier, a Bayesian network, or a k-nearest neighbors (KNN) model. In some embodiments, each of these DL models is constructed based on a convolutional neural network (CNN) architecture, a recurrent neural network (RNN) architecture, or another form of deep neural network (DNN) architecture.

By monitoring and detecting complication events in the background while the display is in the partial-immersive-view mode, the disclosed system can automatically notify the surgeon once such an event has been detected, e.g., by displaying a warning or an alert message on the display screen. In some embodiments, the warning or the alert message can be configured in the form of or in combination with an arrow or other direction indicator to indicate and/or direct the surgeon to the location of the detected off-screen event. Referring to FIG. 2B, assuming that an off-screen complication event has been detected within a region 222 near the lower left corner of the endoscope view, the disclosed system can display a warning in the form of an arrow 224 on display 202 pointing to the location of event region 222.

In some embodiments, upon detecting the off-screen complication event and displaying the associated warning/alert, the disclosed system can automatically change the partial-immersive-view on the display from the current ROI to a new portion of the full endoscope view, which contains the detected off-screen event. Alternatively, the disclosed system can wait for a user response to the event warning/alert and only change the view on the display to the region containing the detected event when an instruction is received from the user in response to the event warning/alert. As yet another alternative, the user can manually change the view from the current immersive view to the portion of the full video images containing the detected event by following an on-screen direction indicator, such as arrow 224. In the example shown in FIG. 2B, the user can reposition the viewing window from ROI 210 to a new ROI 226 (i.e., the dashed rectangular box at the lower left portion of the full image 200) of the same 1920p×1080p size containing event region 222 along the direction indicated by warning arrow 224.

In addition to detecting off-screen complications, the disclosed system can also assist the surgeon in detecting and identifying tool-related off-screen events. In some embodiments, the tool-related off-screen events can include but are not limited to: (1) types of the tools that are present in the off-screen region of the endoscope view; (2) locations of the tools that are present in the off-screen region of the endoscope view; and (3) states of the tools that are present in the off-screen region of the endoscope view. A state of a tool herein can refer to whether the jaws of the tool are closed (clamped down) or open. Monitoring the type, location, and/or state of tools present in the off-screen region of the endoscope view can add a level of safety to the surgical procedure. For example, monitoring the location of a given tool can help in detecting when the tool tip is approaching a critical anatomy in the off-screen region of the endoscope view, or if a given tool is engaged on the tissue in the off-screen region of the endoscope view when it is not supposed to be engaged.

Note that multiple deep-learning models can be constructed to analyze off-screen portions of the video images to detect and identify different types of tools, different states (e.g., open or closed) of a given tool, and different anatomies in the vicinity of an off-screen tool. In various embodiments, each of the multiple deep-learning models for detecting and identifying different tool-related events can include a regression model, a deep neural network-based model, a support vector machine, a decision tree, a Naive Bayes classifier, a Bayesian network, or a k-nearest neighbors (KNN) model. In some embodiments, each of these deep-learning models is constructed based on a convolutional neural network (CNN) architecture, a recurrent neural network (RNN) architecture, or another form of deep neural network (DNN) architecture.

When an off-screen tool-related event is detected that indicates a sufficient level of risk (e.g., when a tool tip is approaching a critical anatomy off-screen), the disclosed system can display a warning or an alert on the screen to prompt the user/surgeon to take appropriate action. In some embodiments, upon detecting the off-screen tool-related event and displaying the associated warning/alert, the disclosed system can automatically change the current partial-immersive-view on the display from the current ROI to a new portion of the endoscope video that contains the detected tool-related event. Alternatively, the disclosed system can wait for a user response to the event warning/alert and only change the view on the display to the region containing the detected tool-related event when an instruction is received from the user in response to the event warning/alert. As yet another alternative, the user can manually change the view from the current immersive view to the portion of the full video images containing the detected tool-related event by following an on-screen direction indicator, such as an arrow. In some embodiments, as an added level of safety, the disclosed system can immediately deactivate functionalities or lock motion of a tool detected in the off-screen region of the endoscope view. Additionally, the disclosed system can generate a critical alert to the surgeon if the detected tool is approaching a critical anatomy in the off-screen region of the endoscope view, thereby allowing the surgeon to take immediate action.

Figure 3:
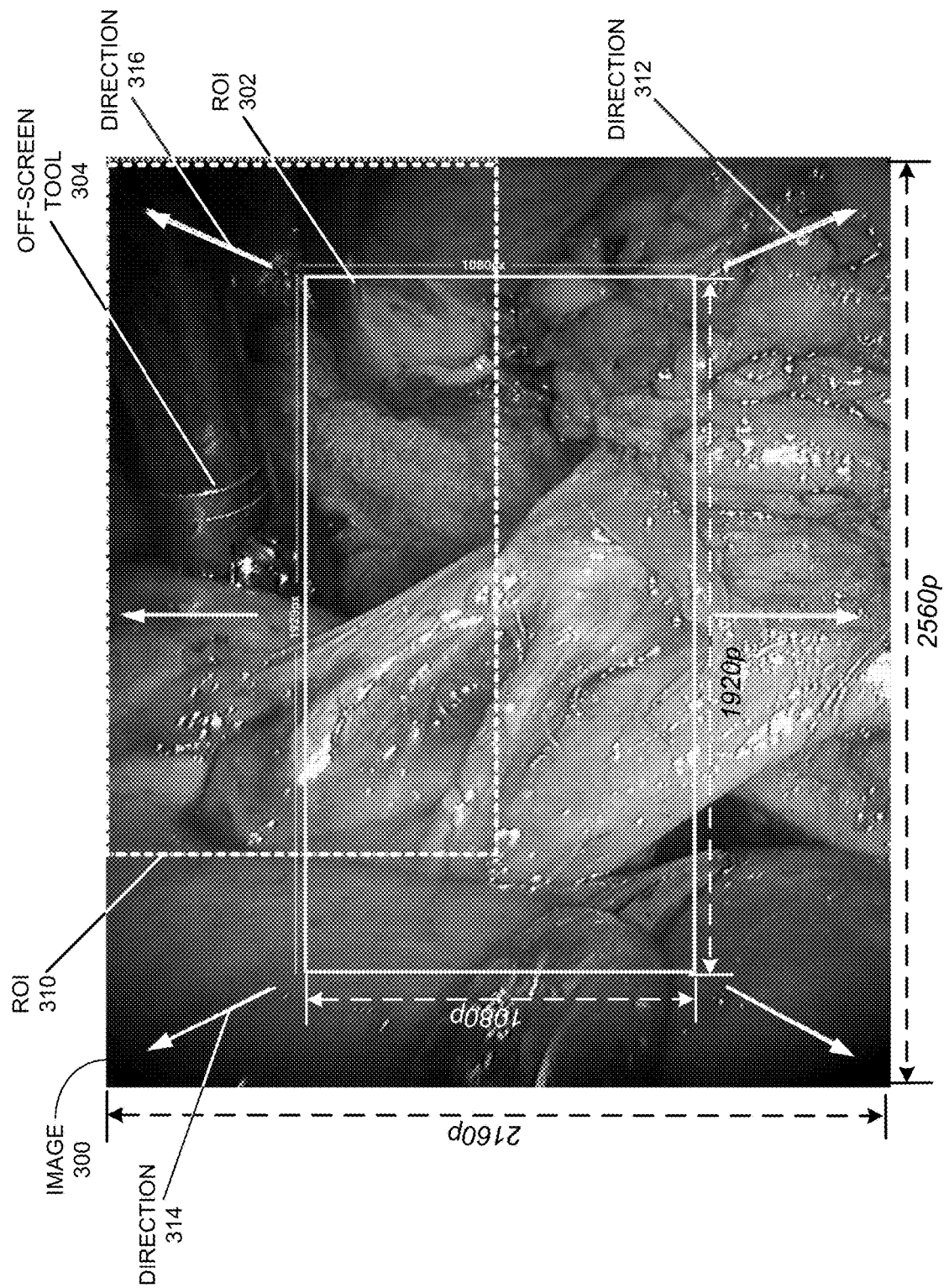
FIG. 3 illustrates an exemplary scenario of detection of an off-screen tool-related event while displaying a full-resolution endoscope video in the partial-immersive-view mode in accordance with some embodiments described herein.

FIG. 3 illustrates an exemplary scenario of detection of an off-screen tool-related event while displaying a full-resolution endoscope video in the partial-immersive-view mode in accordance with some embodiments described herein. As can be seen in FIG. 3, a full-resolution video image 300 represents the full 2560p×2160p resolution endoscope view. A portion of image 300 of 1920p×1080p resolution within the white rectangular box at the center of image 300 represents the current partial-immersive-view/ROI 302 on a display (not explicitly shown) of the same 1920p×1080p native resolution. In one scenario, a surgeon is initially looking at the partial-immersive-view within ROI 302. Next, a tool 304 enters the full endoscope view from the upper right corner but remains in the off-screen portion (i.e., regions outside ROI 302) of image 300, thereby not being visible to the surgeon. However, the disclosed system is configured to detect tool 304 in the off-screen portion of the image 300 and subsequently generate an alert to the surgeon. Upon receiving the alert, the surgeon can take proper action to respond to the alert, such as instructing the system to reposition the viewing window from the current partial-immersive-view within ROI 302 to the upper right region of image 300, or to manually reposition the viewing window. After repositioning the viewing window, the new partial-immersive-view is then displayed inside a new ROI 310 of 1920px 1080p in size indicated by a white rectangular box with dashed lines containing the detected off-screen tool 304. Note that FIG. 3 also shows six short white lines with arrows pointing outward from ROI 302 to six different directions, such as directions 312 and 314. These arrows simply show that the disclosed system can reposition the viewing window from a current ROI to any portion of the full-resolution endoscope video, subsequently making that portion of the endoscope video visible. Hence, the disclosed viewing-window/ROI repositioning technique is not limited to direction 316 and ROI 310 in the upper right portion of the full-resolution endoscope video.

In some embodiments, after an off-screen event (which can be an off-screen complication event or an off-screen tool-related event) has been detected during the partial-immersive-view mode, instead of repositioning the viewing window to make the event visible while staying in the partial-immersive-view mode, the disclosed system can switch the display mode from the partial-immersive-view mode to the full-image-view mode so that the surgeon can observe the entire endoscope view including both the detected event and the current on-screen portion of the endoscope view. This display option is useful when the surgeon does not want to lose track of the current work within the current partial-immersive-view but also wants to see the detected off-screen event. To implement this display option, the system can simply display a warning or an alert message on the screen when the off-screen event is detected. Next, the surgeon can respond to the warning or alert message by manually switching the display mode to the full-image-view mode, e.g., by interacting with a designated icon on the display. In some embodiments, after displaying the warning or alert, the disclosed system can also provide the surgeon with the options to either switch to the full-image-view mode or to reposition the viewing window to the event region while staying in the partial-immersive-view mode. The disclosed system can then display the detected off-screen event using one of the two display options according to a received decision from the surgeon. In yet another embodiment, however, the disclosed system can automatically switch the display to the full-image-view mode when an off-screen event is detected without prompting and waiting for a response from the surgeon. However, this display option generates an abrupt display change on the display that may not be desirable in terms of user experience.

Figure 4:
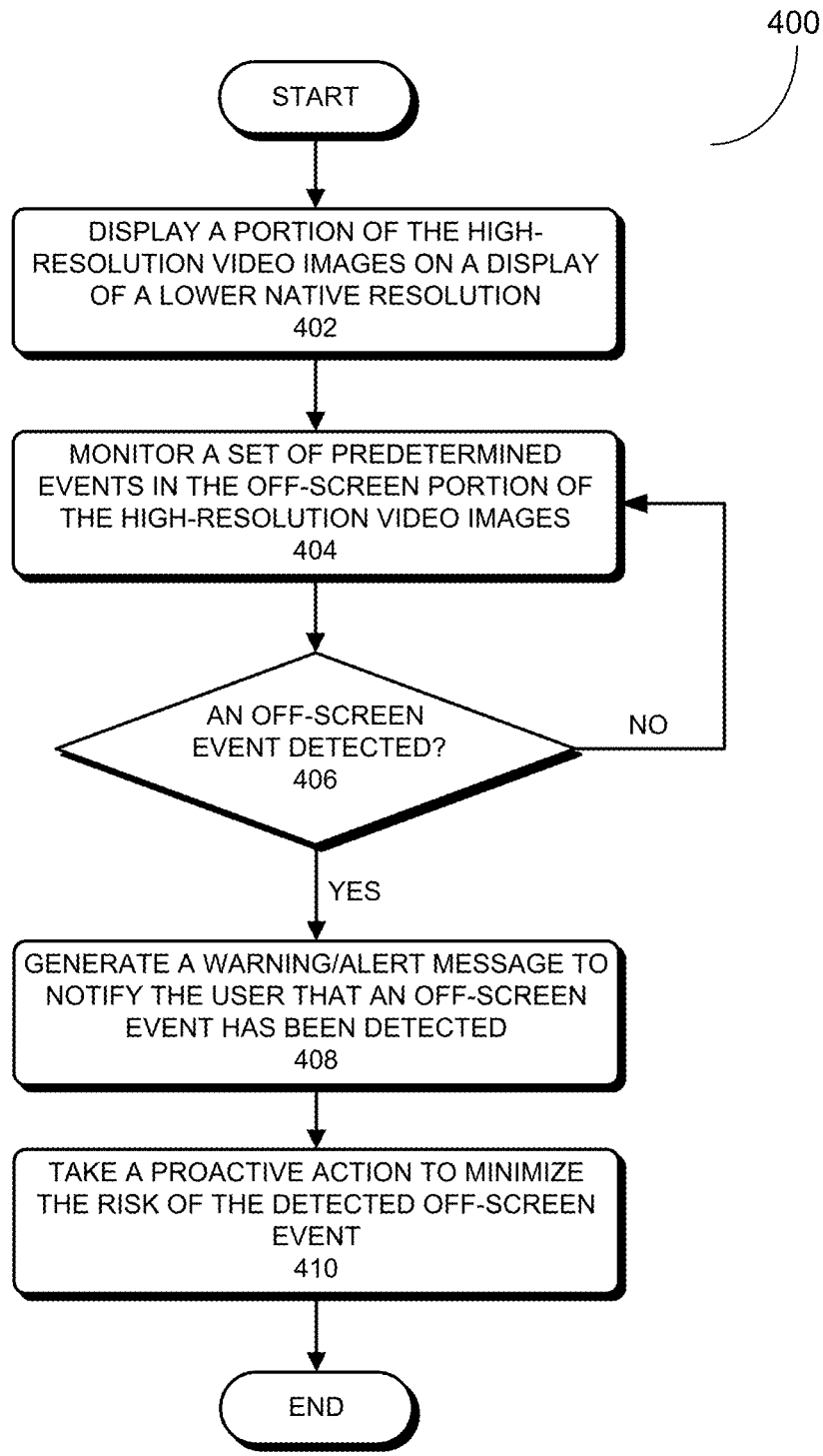
FIG. 4 presents a flowchart illustrating an exemplary process for displaying a high-resolution endoscope video on a display of a lower native resolution in the partial-immersive-view mode while detecting an off-screen event in accordance with some embodiments described herein.

FIG. 4 presents a flowchart illustrating an exemplary process 400 for displaying a high-resolution endoscope video on a display of a lower native resolution in the partial-immersive-view mode while detecting an off-screen event in accordance with some embodiments described herein. In one or more embodiments, one or more of the steps in FIG. 4 may be omitted, repeated, and/or performed in a different order. Accordingly, the specific arrangement of steps shown in FIG. 4 should not be construed as limiting the scope of the technique. Moreover, although described in terms of viewing and processing an endoscope video, the process and the general concept described in conjunction with FIG. 4 is certainly not limited to just endoscope videos. Generally, the process and the general concept described in conjunction with FIG. 4 can be applied to any type of medical procedure videos including, but not limited to, endoscopy videos, laparoscopy videos, arthroscopy videos, and open surgery videos, and to various types of non-surgical medical procedure videos, as well as various types of non-medical-related procedure videos.

As can be seen in FIG. 4, process 400 begins by displaying a portion of the high-resolution endoscope video images on a display of a lower native resolution in the above-described partial-immersive-view mode (step 402). In other words, the portion of the high-resolution video images is being displayed at the original resolution without downsampling that portion of the video images. In some embodiments, the portion of the high-resolution video images being displayed is in the center area of the high-resolution video images. While in the partial-immersive-view mode, process 400 also monitors a set of predetermined events in the off-screen portion of the high-resolution video images (step 404). In some embodiments, one or more deep-learning models can be used to detect each of the set of predetermined events. As described above, the predetermined events that can be detected within the off-screen portion of the high-resolution video images can include complication events such as bleeding or surgical smoke, and tool-related events such as a tool detected in the off-screen portion of the video images or a tool tip detected approaching a critical anatomy in the off-screen portion of the video images.

While monitoring the off-screen region, process 400 also determines if a predetermined off-screen event has been detected (step 406). If not, process 400 returns to step 404 and continues the monitoring operation at step 404. If a predetermined off-screen event is detected, process 400 generates a warning/alert message to notify the user that an off-screen event has been detected (step 408). For example, process 400 can display a warning or an alert message within the partial-immersive-view to prompt the user to take appropriate action. Moreover, the displayed warning or alert message can include a direction indicator to show the user a direction in which the off-screen event was detected. Optionally, after detecting the off-screen event, process 400 can take a proactive action to minimize the risk of the detected off-screen event, e.g., to immediately deactivate functionalities or lock motion of a tool detected off-screen, or to immediately change the view on the display from the current partial-immersive-view/ROI to a new portion of the high-resolution endoscope video that contains the detected off-screen event (step 410).

In addition to automatically detecting off-screen complications and/or tool-related events while displaying the high-resolution endoscope video in the partial-immersive-view mode, the disclosed system can also detect tool movement (assuming a tool is already displayed on the screen) and automatically reposition the viewing window within the full-resolution endoscope view (i.e., the endoscope video images) based on the detected tool movement, thereby keeping the tool tip on-screen and visible to the user. In some embodiments, when the disclosed system initially enters the partial-immersive-view mode, the disclosed system displays the center portion of the high-resolution video images, which typically includes the end/tip of the tool (or simply "tool tip" hereafter) and the movement of the tool tip, which is controlled by the surgeon who is operating the tool on the tissue. However, due to the limited field of view (FOV) of the viewing window, the surgeon can easily move the tool tip away from the center of the screen toward an edge of the partial-immersive-view, and even into the off-screen portion of the endoscope view. As described above, the surgeon can manually reposition the viewing window to another portion of the full-resolution endoscope view so that the tool tip can remain near the center of the display/partial-immersive-view. However, manually moving the viewing window can interfere with the surgical action being performed by the surgeon.

In some embodiments, the disclosed system can be configured to automatically detect the end effector and the tool tip and subsequently track the movement of the tool tip. Note that the tracking can start when the tool tip is inside the viewing window so that the location of the tool tip is continuously tracked in the background. However, the location of the viewing window within the full-resolution endoscope view is not yet changed. Next, when the location of the tool tip is determined to be near an edge of the viewing window and about to go off-screen, the system can select a new ROI of the size of the display within the full-resolution endoscope view based on the current location of the tool tip.

For example, the new region can be determined by minimizing the distance between the center of the new region and the current location of the tool tip. Next, the system can automatically reposition the viewing window from the current location to the new ROI so that the tool tip is brought back to the center or closer to the center of the display. Moreover, after the initial repositioning of the viewing window, the system can start following the movement of the tool tip by continuously adjusting the position of the viewing window based on the movement of the tool tip. Note that when the disclosed function of automatically adjusting the location of the viewing window is engaged, the surgeon no longer needs to manually change the location of the viewing window to follow the movement of the tool tip.

As an alternative embodiment, rather than initially allowing the tool tip to move toward the edge of the display, the disclosed system can start repositioning the viewing window within the full-resolution endoscope view at the same time the system starts tracking the location of the tool tip. More specifically, as the location of the tool tip is continuously tracked, the system also continuously adjusts the location of the viewing window based on the current location of the tool tip to keep the tool tip at or close to the center of the display or at least stay on-screen.

Similarly to detecting and tracking tools in the off-screen portion of the endoscope view, detecting and tracking the tool tip within the on-screen portion of the endoscope view can also be implemented using a deep-learning-based technique. In some embodiments, the disclosed system can be configured to simultaneously detect and track multiple tools both in the on-screen and off-screen portions of the endoscope view. Note that as long as the tool tip remains in the full-resolution (e.g., 2560p×2160p) endoscope view, the disclosed system can keep tracking the tool tip movement and reposition the viewing window to follow the detected tool tip movement. However, the range of this program-controlled repositioning operation is limited by the FOV of the endoscope video. Hence, when the tool tip has moved to the edge of the current FOV of the endoscope video, either a manual or an automatic repositioning of the endoscope camera has to be made to adjust the location of the FOV in the body (e.g., in the direction of the tool tip movement), thereby allowing the disclosed system to continue tracking the tool tip within the full-resolution endoscope video.

Figure 5:
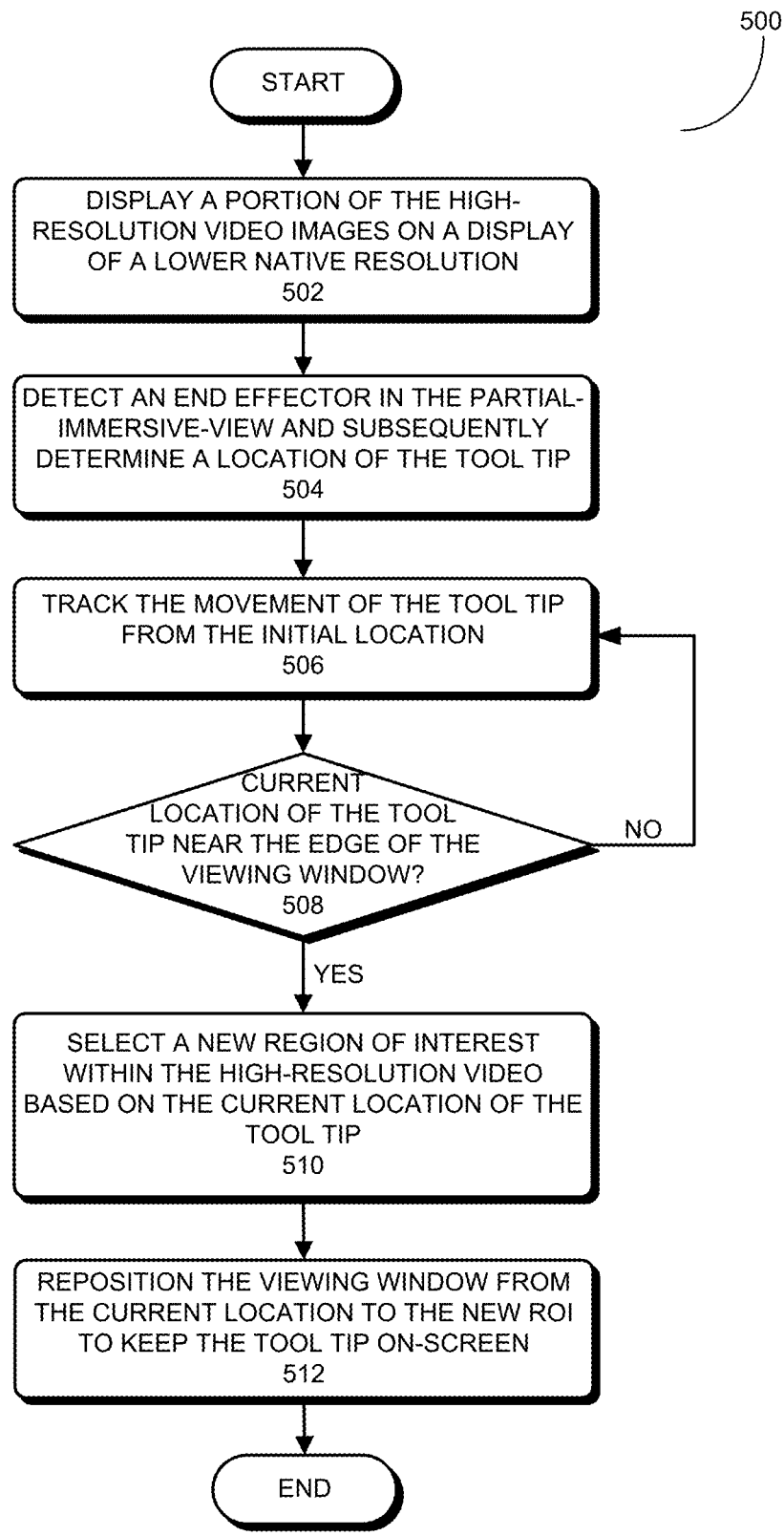
FIG. 5 presents a flowchart illustrating an exemplary process for displaying a high-resolution endoscope video on a display of a lower native resolution in the partial-immersive-view mode while tracking the movement of a surgical tool within the partial-immersive-view in accordance with some embodiments described herein.

FIG. 5 presents a flowchart illustrating an exemplary process 500 for displaying a high-resolution endoscope video on a display of a lower native resolution in the partial-immersive-view mode while tracking the movement of a surgical tool within the partial-immersive-view in accordance with some embodiments described herein. In one or more embodiments, one or more of the steps in FIG. 5 may be omitted, repeated, and/or performed in a different order. Accordingly, the specific arrangement of steps shown in FIG. 5 should not be construed as limiting the scope of the technique. Moreover, although described in terms of viewing and processing an endoscope video, the process and the general concept described in conjunction with FIG. 5 is certainly not limited to just endoscope videos. Generally, the process and the general concept described in conjunction with FIG. 5 can be applied to any type of medical procedure videos including, but not limited to, endoscopy videos, laparoscopy videos, arthroscopy videos, and open surgery videos.

As can be seen in FIG. 5, process 500 begins by displaying a portion of the high-resolution endoscope video images on a display of a lower resolution in the above-described partial-immersive-view mode (step 502). In other words, the portion of the high-resolution video images is being displayed at the original resolution without downsampling that portion of the video images. In some embodiments, the portion of the high-resolution video images being displayed is in the center area of the high-resolution video images. While in the partial-immersive-view mode, process 500 also detects an end effector in the partial-immersive-view and subsequently determines an initial location of the tool tip (step 504). In some embodiments, the system uses one or more deep-learning models to detect the presence of one or more surgical tools. After determining the initial location of the tool tip, the systems start tracking a movement of the tool tip from the initial location (step 506).

While tracking the movement of the tool tip, the system continuously determines whether the current location of the tool tip is near an edge of the viewing window and therefore about to go off-screen (step 508). For example, the system can set a threshold distance that can be compared with a distance between the current tool tip location and the edge of the viewing window. If the distance to the edge of the viewing window is below the threshold distance, the system can consider that the tool tip is about to move off-screen. Then, the system selects a new region of interest (ROI) within the high-resolution endoscope video based on the current location of the tool tip (step 510). Otherwise, if the system determines that the tool tip is not about to go off-screen, the system returns to step 506 and continues tracking the movement of the tool tip. Next, the system automatically repositions the viewing window from the current location to the new ROI so that the tool tip is brought back to the center or closer to the center of the display (step 512). Moreover, after the initial repositioning the viewing window, the system can optically follows the movement of the tool tip by continuously adjusting the position of the viewing window based on the detected movement of the tool tip.

In addition to detecting surgical tool movements and automatically repositioning the viewing window based on the detected tool movements while displaying the high-resolution endoscope video in the partial-immersive-view mode, the disclosed system can also be integrated with an eye-tracking module for detecting and tracking the surgeon's gaze and automatically repositioning the viewing window based on the location of the surgeon's gaze/focus on the display. In some embodiments, the eye-tracking module of the disclosed system can determine the location of the gaze, i.e., the location on the display where the surgeon is currently looking (i.e., the focal point of the gaze) based on analyzing the eye and head movements of the surgeon. For example, the disclosed system can include a camera installed on the display or near the display pointing toward the surgeon, which can capture videos of the surgeon's eyes and head during the surgical procedure. Hence, the eye-tracking module of the disclosed system can process the captured video images of the surgeon's eyes and head to determine locations of the surgeon's gaze on the display.

In some embodiments, if the location of the surgeon's gaze on the display is determined to have changed, the disclosed system repositions the viewing window to a new ROI within the high-resolution endoscope view. After repositioning the viewing window to the new ROI, the partial-immersive-view can be centered around the new location of the surgeon's gaze on the display. Moreover, as the surgeon's gaze moves, e.g., in one of the vertical, horizontal, or angular directions, the eye-tracking module of the disclosed system can "follow" the gaze by continuously determining the current location of the surgeon's gaze on the display, and continuously repositioning the viewing window so that it is centered around the current location of the surgeon's gaze, thereby creating a smooth movement of the viewing window that follows the surgeon's gaze. In some embodiments, the eye-tracking module includes one or more deep-learning models that can be used to determine the location of the surgeon's gaze by analyzing the captured images of the surgeon's eyes and head. Each of these deep-learning models can include a regression model, a deep neural network-based model, a support vector machine, a decision tree, a Naive Bayes classifier, a Bayesian network, or a k-nearest neighbors (KNN) model. In some embodiments, each of these deep-learning models is constructed based on a convolutional neural network (CNN) architecture, a recurrent neural network (RNN) architecture, or another form of deep neural network (DNN) architecture.

As can be seen, by performing automatic gaze tracking and viewing window repositioning, the disclosed system allows the surgeon to directly control and move the viewing window within the high-resolution endoscope video by simply changing the gaze. In this manner, the current partial-immersive-view can stay centered around the location on the display corresponding to the surgeon's gaze. Note that using the gaze to directly control the position of the viewing window relieves the surgeon of having to manually reposition the viewing window. Moreover, when using the gaze to control the position of the viewing window, the above-described tool-tracking-based repositioning functionality can be disabled. Furthermore, in cases when the surgical tools in the FOVs are not moving but the surgeon wants to see another region of the high-resolution video, using the gaze to control the position of the viewing window provides a straightforward but highly effective solution.

Figure 6:
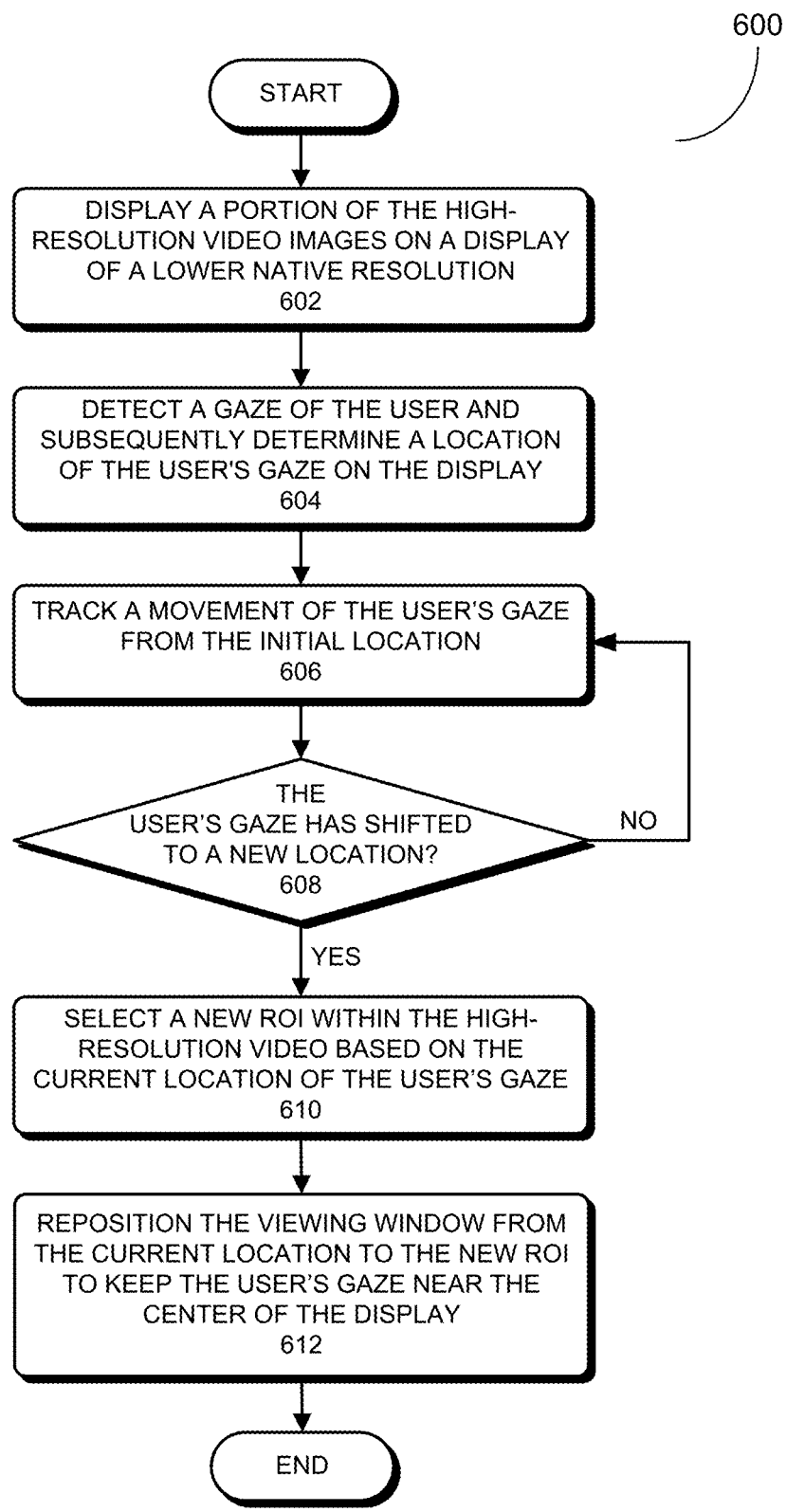
FIG. 6 presents a flowchart illustrating an exemplary process for displaying a high-resolution endoscope video on a display of a lower native resolution in the partial-immersive-view mode while tracking a user's focus/gaze on the display in accordance with some embodiments described herein.

FIG. 6 presents a flowchart illustrating an exemplary process 600 for displaying a high-resolution endoscope video on a display of a lower native resolution in the partial-immersive-view mode while tracking a user's focus/gaze on the display in accordance with some embodiments described herein. In one or more embodiments, one or more of the steps in FIG. 6 may be omitted, repeated, and/or performed in a different order. Accordingly, the specific arrangement of steps shown in FIG. 6 should not be construed as limiting the scope of the technique. Moreover, although described in terms of viewing and processing an endoscope video, the process and the general concept described in conjunction with FIG. 6 is certainly not limited to just endoscope videos. Generally, the process and the general concept described in conjunction with FIG. 6 can be applied to any type of medical procedure videos including, but not limited to, endoscopy videos, laparoscopy videos, arthroscopy videos, and open surgery videos.

As can be seen in FIG. 6, process 600 begins by displaying a portion of the full-resolution endoscope video images on a display of a lower resolution in the above-described partial-immersive-view mode (step 602). In other words, the portion of the high-resolution video images is being displayed at the original resolution without downsampling that portion of the video images. In some embodiments, the portion of the high-resolution video images being displayed is in the center area of the high-resolution video images. While in the partial-immersive-view mode, process 600 also detects a gaze of the user and subsequently determines an initial location of the user's gaze (e.g., the focal point of the user's gaze) on the display (step 604). In some embodiments, the system uses one or more deep-learning models to determine the location of user's gaze on the display by analyzing the captured images of the user's eyes and head.

After determining the initial location of the user's gaze, the system starts tracking a movement of the user's gaze from the initial location, e.g., by using a deep-learning-based gaze-tracking technique (step 606).

Next, the system determines if the user's gaze has shifted from a previously determined location to a new location (step 608). If not, the system returns to step 606 and continues tracking the user's gaze. However, if the system determines that the user's gaze has shifted, the system selects a new region of interest (ROI) within the high-resolution video based on the current location of the user's gaze (step 610). Next, the system automatically repositions the viewing window from the current location to the new ROI to keep the user's gaze near the center of the display (step 612).

Note that each high-resolution endoscope view has a finite range. For the above-described repositioning processes, either performed manually or automatically, the range of repositioning of the viewing window is limited by the dimensions of the endoscope view. Hence, when the new ROI is approaching the boundary of the endoscope view, the corresponding viewing window starts to go beyond the boundary of the endoscope view. This is an indication that the current endoscope view is not sufficient to handle the movements of the surgical procedure, and the endoscope camera needs to be moved to a new view/location. In some embodiments, when the location of the new ROI exceeds a certain minimum distance to the boundary of the endoscope view, the disclosed system can generate an alert to the user to reposition the endoscope camera. After a proper repositioning of the endoscope camera, the new ROI should remain inside the adjusted boundary of the endoscope view so that the subsequent repositioning of the viewing window can proceed normally.

Figure 7:
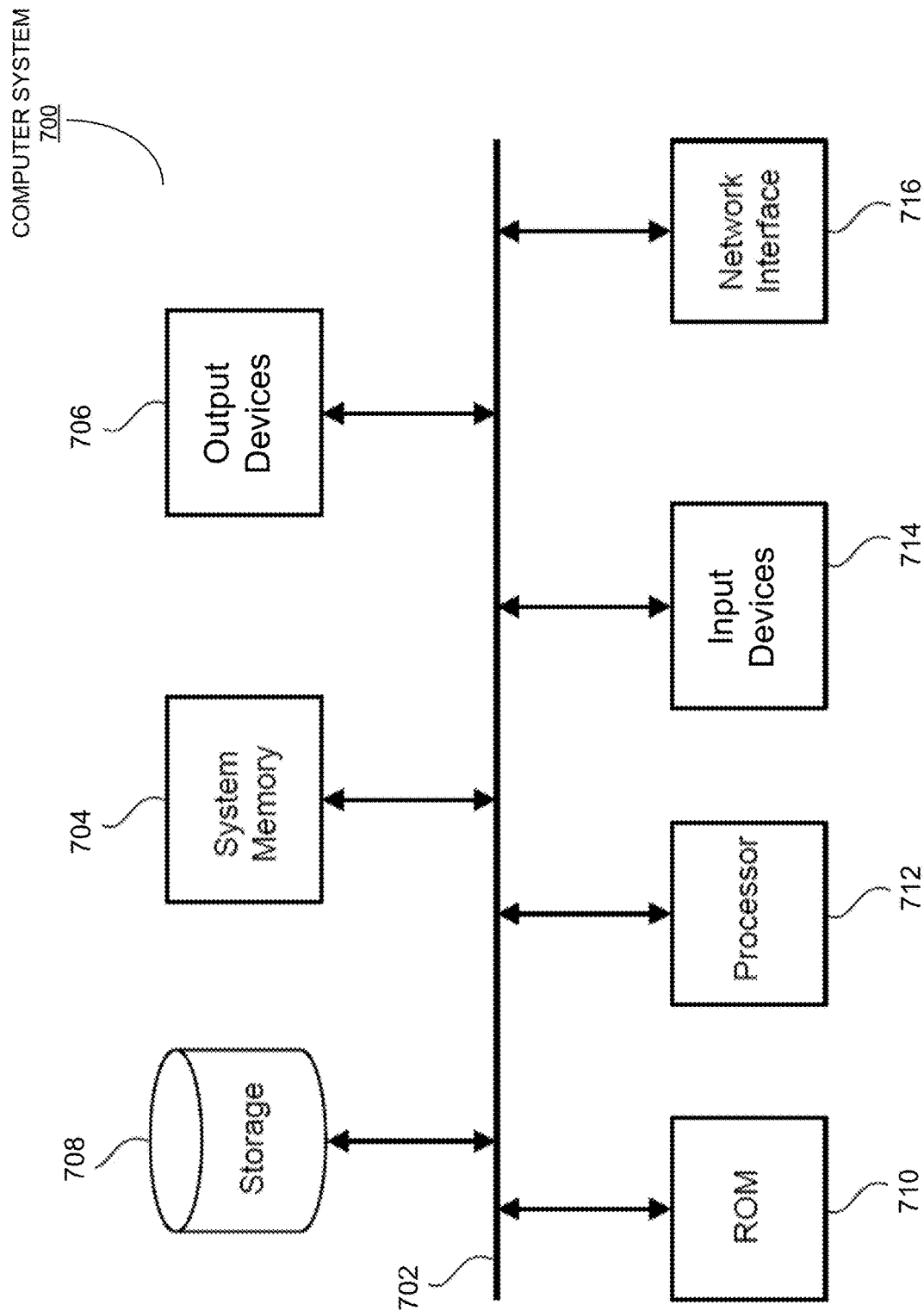
FIG. 7 conceptually illustrates a computer system with which some embodiments of the subject technology can be implemented.

FIG. 7 conceptually illustrates a computer system with which some embodiments of the subject technology can be implemented. Computer system 700 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 700 includes a bus 702, processing unit(s) 712, a system memory 704, a read-only memory (ROM) 710, a permanent storage device 708, an input device interface 714, an output device interface 706, and a network interface 716. In some embodiments, computer system 700 is a part of a robotic surgical system.

Bus 702 collectively represents all system, peripheral, and chipset buses that communicatively connect the numerous internal devices of computer system 700. For instance, bus 702 communicatively connects processing unit(s) 712 with ROM 710, system memory 704, and permanent storage device 708.

From these various memory units, processing unit(s) 712 retrieves instructions to execute and data to process in order to execute various processes described in this patent disclosure, including the above-described processes of displaying a high-resolution endoscope video on a display of a lower native resolution in the partial-immersive-view mode while detecting an off-screen event, while tracking the movement of a surgical tool, or while tracking a user's focus/gaze on the display in conjunction with FIGS. 2B and 3-6. The processing unit(s) 712 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 712 can be a single processor or a multi-core processor in different implementations.

ROM 710 stores static data and instructions that are needed by processing unit(s) 712 and other modules of the computer system. Permanent storage device 708, on the other hand, is a read-and-write memory device. This device is a non-volatile memory unit that stores instructions and data even when computer system 700 is off. Some implementations of the subject disclosure use a mass-storage device (such as a magnetic or optical disk and its corresponding disk drive) as permanent storage device 708.

Other implementations use a removable storage device (such as a floppy disk, flash drive, and its corresponding disk drive) as permanent storage device 708. Like permanent storage device 708, system memory 704 is a read-and-write memory device. However, unlike storage device 708, system memory 704 is a volatile read-and-write memory, such as a random access memory. System memory 704 stores some of the instructions and data that the processor needs at runtime. In some implementations, various processes described in this patent disclosure, including the processes of displaying a high-resolution endoscope video on a display of a lower native resolution in the partial-immersive-view mode while detecting an off-screen event, while tracking the movement of a surgical tool, or while tracking a user's focus/gaze on the display in conjunction with FIGS. 2B and 3-6, are stored in system memory 704, permanent storage device 708, and/or ROM 710. From these various memory units, processing unit(s) 712 retrieve instructions to execute and data to process in order to execute the processes of some implementations.

Bus 702 also connects to input and output devices 714 and 706. Input devices 714 enable the user to communicate information to and select commands for the computer system. Input devices 714 can include, for example, alphanumeric keyboards and pointing devices (also called "cursor control devices"). Output devices 706 enable, for example, the display of images generated by computer system 700. Output devices 706 can include, for example, printers and display devices, such as cathode ray tubes (CRT) or liquid crystal displays (LCD). Some implementations include devices such as a touchscreen that functions as both input and output devices.

Finally, as shown in FIG. 7, bus 702 also couples computer system 700 to a network (not shown) through a network interface 716. In this manner, the computer can be a part of a network of computers (such as a local area network ("LAN"), a wide area network ("WAN"), an intranet, or a network of networks, such as the Internet. Any or all components of computer system 700 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for displaying video images of a surgical video captured at a first resolution on a screen of a surgical system having a second resolution lower than the first resolution, the method comprising:
    for each video image captured at the first resolution, selecting a first portion of the video image having the same resolution as the second resolution of the screen, wherein selecting the first portion of the video image includes keeping the first portion of the video image substantially centered on a tool-tip of a surgical tool displayed in the video image;
    displaying the first portion of the video image on the screen without changing the resolution of the first portion of the video image;
    while displaying the first portion of the video image, monitoring a second portion of the video image not being displayed on the screen for a set of predetermined events, wherein the second portion of the video image is not visible to the user; and
    when a predetermined event in the set of predetermined events is detected in the second portion of the video image, generating an alert to notify the user that an off-screen event has been detected,
    wherein when the off-screen event is detected, immediately changing the view on the screen from the first portion of the video image to the full video image of the surgical video displayed at a reduced resolution to make both the first portion of the video image and the detected off-screen event visible to the user on the screen.

2. The computer-implemented method of claim 1,
    wherein the first resolution is greater than the second resolution in both the horizontal and the vertical dimensions; and
    wherein the first portion of the video image is substantially the center portion of the video image.

3. The computer-implemented method of claim 1, wherein while displaying the first portion of the video image, the first portion of the video image occupies the full display area of the screen without leaving any blank space on the screen.

4. The computer-implemented method of claim 1, wherein monitoring the second portion of the video image for the set of predetermined events includes using one or more machine-learning models to process the second portion of the video image in order to detect each of the set of predetermined events.

5. The computer-implemented method of claim 1, wherein generating the alert to notify the user that an off-screen event has been detected includes displaying a warning message on the screen to prompt the user to take appropriate action.

6. The computer-implemented method of claim 1, wherein the alert on the screen includes a direction indicator to show the user a direction in which the off-screen event was detected.

7. The computer-implemented method of claim 1, wherein when the off-screen event is detected, the method further comprises immediately changing the view on the screen from the first portion of the video image to a third portion of the video image, which contains the detected off-screen event.

8. The computer-implemented method of claim 7, wherein the third portion of the video image overlaps with the first portion and the second portion of the video image and has the same size as the first portion of the video image.

9. The computer-implemented method of claim 1, wherein after generating the alert to notify the user that an off-screen event has been detected, the method further comprises:
    providing the user with a selection option to either change the view on the screen from the first portion of the video image to another portion of the video image containing the detected off-screen event or change the view on the screen from the first portion of the video image to the full video image displayed at a reduced resolution;
    receiving a user selection in response to the selection option; and
    changing the view on the screen based on the received user selection to make the detected off-screen event visible to the user.

10. The computer-implemented method of claim 1, wherein after generating the alert to notify the user that an off-screen event has been detected, the method further comprises allowing the user to manually change the view on the screen from the first portion of the video image to another portion of the video image containing the detected off-screen event in response to the alert.

11. The computer-implemented method of claim 1, wherein the set of predetermined events includes surgical smoke and bleeding.

12. The computer-implemented method of claim 1, wherein the set of predetermined events includes a set of surgical tool-related events, which further includes: (1) whether the jaws of a surgical tool detected off-screen are closed or open; and (2) whether a tip of a surgical tool detected off-screen is too close to a critical anatomy.

13. The computer-implemented method of claim 12, wherein if the detected predetermined event is one of the set of surgical tool-related events, the method further comprises immediately deactivating functionalities or locking motion of a surgical tool associated with the detected surgical tool-related event.

14. The computer-implemented method of claim 1, wherein the surgical video is one of:
    an endoscopic surgery video;
    a laparoscopic surgery video;
    a robotic surgery video; and
    an open surgery video.

15. The computer-implemented method of claim 1, wherein keeping the first portion of the video image substantially centered on the tool-tip of the surgical tool displayed in the video image includes:
    detecting, using a machine-learning-based technique, the surgical tool in the video image;

determining a location of the tool-tip of the detected surgical tool; and positioning the first portion of the video image based on the location of the tool-tip.

16. A system for displaying a surgical video, comprising:
one or more processors; and
a screen having a native resolution,
wherein the one or more processors are configured to:
- receive a surgical video comprising a sequence of video images captured at a first resolution for display on the screen, wherein the first resolution is greater than the native resolution of the screen;
- for each video image in the sequence of video images, select a first portion of the video image having the same resolution as the native resolution of the screen to be displayed on the screen without changing the resolution of the first portion of the video image, wherein selecting the first portion of the video image includes keeping the first portion of the video image substantially centered on a tool-tip of a surgical tool displayed in the video image;
- while displaying the first portion of the video image, monitor a second portion of the video image not being displayed on the screen for a set of predetermined events, wherein the second portion of the video image is not visible to the user; and
- if a predetermined event in the set of predetermined events is detected in the second portion of the video image, generate an alert to notify the user that an off-screen event has been detected,
- wherein when the off-screen event is detected, immediately change the view on the screen from the first portion of the video image to the full video image of the surgical video displayed at a reduced resolution to make both the first portion of the video image and the detected off-screen event visible to the user on the screen.

17. The system of claim 16, wherein when the off-screen event is detected, the one or more processors are further configured to immediately change the view on the screen from the first portion of the video image to a third portion of the video image, which contains the detected off-screen event.

18. The system of claim 16, wherein after generating the alert to notify the user that an off-screen event has been detected, the one or more processors are further configured to:
- provide the user with a selection option to either change the view on the screen from the first portion of the video image to another portion of the video image containing the detected off-screen event or change the view on the screen from the first portion of the video image to the full video image displayed at a reduced resolution;
- receive a user selection in response to the selection option; and
- change the view on the screen based on the received user selection to make the detected off-screen event visible to the user.

* * * * *